(12) United States Patent
Miyachi et al.

(10) Patent No.: US 12,279,751 B2
(45) Date of Patent: Apr. 22, 2025

(54) IMAGE FIBER, ENDOSCOPE HAVING IMAGE FIBER, AND ENDOSCOPE SYSTEM HAVING ENDOSCOPE

(71) Applicant: Fujikura Ltd., Tokyo (JP)

(72) Inventors: Masami Miyachi, Chiba (JP); Manabu Kudo, Chiba (JP)

(73) Assignee: Fujikura Ltd., Tokyo (JP)

( * ) Notice: Subject to any disclaimer, the term of this patent is extended or adjusted under 35 U.S.C. 154(b) by 498 days.

(21) Appl. No.: 17/628,047

(22) PCT Filed: Jun. 25, 2020

(86) PCT No.: PCT/JP2020/024942
§ 371 (c)(1),
(2) Date: Jan. 18, 2022

(87) PCT Pub. No.: WO2021/014876
PCT Pub. Date: Jan. 28, 2021

(65) Prior Publication Data
US 2022/0257098 A1     Aug. 18, 2022

(30) Foreign Application Priority Data
Jul. 19, 2019   (JP) ................................. 2019-134005

(51) Int. Cl.
*A61B 1/00*     (2006.01)
*A61B 1/04*     (2006.01)
(Continued)

(52) U.S. Cl.
CPC ........ *A61B 1/00167* (2013.01); *A61B 1/0017* (2013.01); *A61B 1/042* (2013.01);
(Continued)

(58) Field of Classification Search
CPC . A61B 1/042; A61B 1/00165; A61B 1/00167; A61B 1/0017; A61B 1/07; A61B 1/0607; A61B 2018/2261; A61B 2090/306; G02B 6/06; G02B 6/001; G02B 23/26; G02B 6/02
See application file for complete search history.

(56) References Cited

U.S. PATENT DOCUMENTS 5,471,553 A * 11/1995 Teshima .................. B29C 48/34
                                                    385/115
5,479,550 A * 12/1995 Nishioka ................. C03B 37/15
                                                    385/116
(Continued)

FOREIGN PATENT DOCUMENTS

JP        2010-169715 A       8/2010
JP        2013-039178 A       2/2013

*Primary Examiner* — Chad H Smith
*Assistant Examiner* — Kirsten D. Endresen
(74) *Attorney, Agent, or Firm* — Osha Bergman Watanabe & Burton LLP

(57) ABSTRACT

An image fiber includes: a plurality of cores; a cladding that integrally encloses the plurality of cores; a light guide fiber that propagates illumination light; and a light guide layer that covers an entire periphery of an external peripheral surface of the cladding and that is in contact with an external peripheral surface of the light guide fiber. The light guide layer is capable of propagating the illumination light.

14 Claims, 3 Drawing Sheets

(51) Int. Cl.
*G02B 6/02* (2006.01)
*G02B 6/06* (2006.01)
*G02B 23/26* (2006.01)

(52) U.S. Cl.
CPC ................. *G02B 6/02* (2013.01); *G02B 6/06* (2013.01); *G02B 23/26* (2013.01)

(56) References Cited

U.S. PATENT DOCUMENTS

| | | | |
|---|---|---|---|
| 5,608,835 A * | 3/1997 | Ono | G02B 6/03605 385/126 |
| 2007/0183727 A1* | 8/2007 | Strack | G02B 6/4475 385/100 |
| 2014/0152789 A1 | 6/2014 | Hu et al. | |
| 2015/0241634 A1 | 8/2015 | Coutard et al. | |
| 2015/0268414 A1* | 9/2015 | Hayashi | H04B 10/25891 385/127 |
| 2018/0172926 A1 | 6/2018 | Hodge | |

* cited by examiner

IMAGE FIBER, ENDOSCOPE HAVING IMAGE FIBER, AND ENDOSCOPE SYSTEM HAVING ENDOSCOPE

TECHNICAL FIELD

The present invention relates to an image fiber, an endoscope having the image fiber, and an endoscope system having the endoscope.

BACKGROUND

An endoscope including an elongated insertion portion is widely used in, for example, an industrial field or a medical field. When the insertion portion is inserted into a subject, an object in the subject is observed. Examples of the subject include a structure such as an engine and a body cavity.

For example, Patent Literature 1 discloses an image fiber cable that is mounted in an insertion portion of an endoscope and through which imaging light and illumination light propagate. The imaging light is light representing an image of an object, and the illumination light is light irradiating the object at the time of observing the object including image photographing. The image fiber cable includes an image fiber, a plurality of light guide fibers disposed on an external peripheral surface of the image fiber, and a tape spirally wound around the light guide fibers. The imaging light propagates through the image fiber, and illumination light propagates through the light guide fibers. The plurality of light guide fibers is secured to the image fiber by the tape.

[Patent Literature 1] JP 2010-169715 A

In the image fiber cable disclosed in Patent Literature 1, the plurality of light guide fibers is disposed concentrically, and a gap is generated between two adjacent circular light guide fibers. Therefore, there is a concern that uneven irradiation occurs in the illumination light emitted from the plurality of light guide fibers toward the object, and suppression of uneven irradiation is desired.

SUMMARY

One or more embodiments of the present invention provide an image fiber capable of suppressing uneven irradiation of illumination light, an endoscope having the image fiber, or an endoscope system having the endoscope.

In one or more embodiments, an image fiber of the present invention includes: a plurality of cores; a cladding integrally enclosing the plurality of cores; at least one light guide fiber through which illumination light propagates; and a light guide layer covering an external peripheral surface of the cladding over an entire periphery and in contact with an external peripheral surface of the light guide fiber, the light guide layer being capable of propagating the illumination light from the light guide fiber.

In such an image fiber, since the illumination light propagates through the light guide fiber and can propagate from the light guide fiber to the light guide layer, the illumination light can propagate through the entire region of the cross-section of the light guide layer covering the external peripheral surface of the cladding over the entire periphery. Therefore, with the image fiber according to one or more embodiments of the present invention, uneven irradiation of the illumination light can be suppressed.

In addition, in one or more embodiments, the light guide layer has a cover layer made of resin, a refractive index of the cover layer is higher than a refractive index of the cladding and is equal to or higher than a refractive index of the light guide fiber, and the light guide fiber is disposed in at least a part of an inside of the cover layer along a longitudinal direction of the light guide layer.

The flexibility of the cover layer made of resin is generally superior to the flexibility of a layer made of glass. Therefore, the cover layer is resistant to bending and is in close contact with the external peripheral surface of the cladding or the like to be in a state of being more stably disposed. Thus, displacement of the emission position of the illumination light is further suppressed, and the illumination light can be more stably emitted toward the object. Therefore, with the image fiber, the illumination light can be emitted more stably.

In addition, when the refractive index of the cover layer is higher than the refractive index of the cladding, propagation of the illumination light from the cover layer to the cladding can be suppressed. Therefore, with the image fiber, waste of the illumination light can be suppressed. In addition, when the refractive index of the cover layer is equal to or higher than the refractive index of the light guide fiber, the illumination light easily propagates from the light guide fiber to the cover layer, a part of the illumination light propagates from the light guide fiber to the cover layer and further propagates through the cover layer, and in addition, another part of the illumination light can propagate through the light guide fiber. Therefore, with the image fiber, the illumination light can be more efficiently propagated to the light guide fiber by the cover layer. In addition, since the illumination light propagates through the cover layer and is emitted from the cover layer, the emission range of the illumination light can be expanded as compared with the case where the illumination light is emitted only from the light guide fiber, and uneven irradiation of the illumination light can be suppressed.

In addition, when the light guide fiber is disposed in at least a part of the inside of the cover layer, displacement of the light guide fiber with respect to the cover layer is suppressed, and the light guide fiber is in a state of being stably disposed. In addition, when the light guide fiber is disposed in at least a part of the inside of the cover layer, the illumination light can propagate from the entire periphery of the external peripheral surface of the light guide fiber to the cover layer. Therefore, with the image fiber, uneven irradiation of the illumination light can be suppressed.

In addition, in general, the thickness of the cover layer is controlled at the time of manufacturing the image fiber and can be easily reduced. Therefore, with the image fiber, the image fiber can be easily reduced in diameter.

In addition, since the light guide fiber is disposed not on the external peripheral surface of the cover layer but in at least a part of the inside of the cover layer, with the image fiber, an increase in diameter of the image fiber can be prevented. In addition, in general, the light guide fiber through which the illumination light propagates has light propagation efficiency superior to that of the cover layer. Therefore, with the image fiber, brighter illumination light can be emitted.

In addition, in one or more embodiments, the light guide fiber is disposed from one end to the other end of the cover layer along the longitudinal direction of the light guide layer.

In this case, the cover layer can efficiently propagate the illumination light from one end to the other end of the cover layer by the light guide fiber. Thus, a part of the illumination light can propagate through the cover layer, and in addition, another part of the illumination light can propagate through the light guide fiber. Therefore, with the image fiber, the illumination light can be efficiently propagated, and uneven irradiation of the illumination light can be suppressed.

In addition, in one or more embodiments, the light guide layer further has an outer low refractive index layer covering the external peripheral surface of the cover layer over an entire periphery and a refractive index of the outer low refractive index layer is lower than the refractive index of the cover layer.

In this case, the illumination light propagating through the cover layer is easily confined in the cover layer by the outer low refractive index layer, and can propagate through the cover layer in a state where leakage from the cover layer to the outside of the image fiber is suppressed. Therefore, with the image fiber, the illumination light can be more efficiently propagated.

In addition, in one or more embodiments, the light guide layer has a quartz layer having a refractive index higher than the refractive index of the cladding and equal to or higher than the refractive index of the light guide fiber, and the light guide fiber is disposed on at least a part of an external peripheral surface of the quartz layer along a longitudinal direction of the light guide layer.

At the time of manufacturing an image fiber, a plurality of core-cladding optical fibers is generally inserted into a quartz tube in a bundled state, melted after the insertion, and integrated together with the quartz tube, and the quartz tube becomes a quartz layer. Thus, even when bending occurs in the image fiber, the quartz layer, which is integral with the cladding, is in a state of being stably disposed.

In addition, when the refractive index of the quartz layer is higher than the refractive index of the cladding, propagation of the illumination light from the quartz layer to the cladding can be suppressed. Therefore, with the image fiber, waste of the illumination light can be suppressed. In addition, when the refractive index of the quartz layer is equal to or higher than the refractive index of the light guide fiber, the illumination light easily propagates from the light guide fiber to the quartz layer, a part of the illumination light propagates from the light guide fiber to the quartz layer and further propagates through the quartz layer, and in addition, another part of the illumination light can propagate through the light guide fiber. Therefore, with the image fiber, the illumination light can be efficiently propagated to the quartz layer by the light guide fiber, and the illumination light is propagated through the quartz layer and emitted from the quartz layer. Therefore, the emission range of the illumination light can be expanded as compared with the case where the illumination light is emitted only from the light guide fiber, and uneven irradiation of the illumination light can be suppressed.

In addition, when the light guide fiber is disposed on at least a part of the external peripheral surface of the quartz layer along the longitudinal direction of the light guide layer, a part of the illumination light propagating through the light guide fiber propagates from the light guide fiber to the quartz layer and can propagate through the quartz layer. Therefore, with the image fiber, uneven irradiation of the illumination light can be suppressed.

In addition, in one or more embodiments, the light guide fiber is disposed from one end to the other end of the quartz layer along the longitudinal direction of the quartz layer.

In this case, the light guide layer can efficiently propagate the illumination light from one end to the other end of the quartz layer by the light guide fiber. Therefore, with the image fiber, the illumination light can be efficiently propagated.

In addition, in one or more embodiments, the light guide layer further has an inner low refractive index layer disposed between the cladding and the quartz layer, and a refractive index of the inner low refractive index layer is lower than the refractive index of the cladding.

In this case, the illumination light is easily confined in the quartz layer by the inner low refractive index layer, and can propagate through the quartz layer in a state where leakage from the quartz layer to the cores and the cladding is suppressed. Therefore, with the image fiber, the illumination light can be more efficiently propagated.

In addition, in one or more embodiments, the quartz layer has at least one groove provided in at least a part of an external peripheral surface of the quartz layer along a longitudinal direction of the light guide layer, and at least a part of the light guide fiber in a radial direction is disposed in the groove.

When at least a part of the light guide fiber in the radial direction is disposed in the groove, the light guide fiber is in a state of being stably disposed with respect to the quartz layer. Thus, even when bending occurs in the image fiber, displacement of the emission position of the illumination light is further suppressed, and the illumination light can be more stably emitted toward the object. Therefore, with the present image fiber, the illumination light can be emitted stably.

In addition, an endoscope according to one or more embodiments of the present invention includes an insertion portion to be inserted into a subject, and the image fiber according to any one of the above to be disposed in an internal space of the insertion portion.

In the endoscope, the uneven irradiation of the illumination light can be suppressed, and the endoscope can irradiate the object in the subject with the illumination light with suppressed uneven irradiation.

In addition, an endoscope system according to one or more embodiments of the present invention includes: the endoscope described above; a light source portion that emits the illumination light; an optical system that propagates the illumination light emitted from the light source portion toward the light guide fiber, and captures an image of imaging light that is reflected light reflected from an object irradiated with the illumination light and has propagated through the cores; and a display portion that displays an image on the basis of the imaging light captured by the optical system.

In the endoscope system, the endoscope can irradiate the object with the illumination light with suppressed uneven irradiation, the display portion can display the image of the object in which the uneven irradiation is suppressed.

As described above, one or more embodiments of the present invention provide an image fiber capable of suppressing uneven irradiation of illumination light, an endoscope having the image fiber, or an endoscope system having the endoscope.

DETAILED DESCRIPTION

Embodiments of an image fiber according to the present invention will be described below in detail with reference to the drawings. The embodiments illustrated below are for facilitating the understanding of the present invention, and are not for limiting the interpretation of the present invention. The present invention can be changed or modified without departing from the spirit. In addition, in the present invention, components in the following exemplary embodiments may be appropriately combined. Note that, for easy understanding, some parts may be exaggerated in each drawing.

Figure 1:
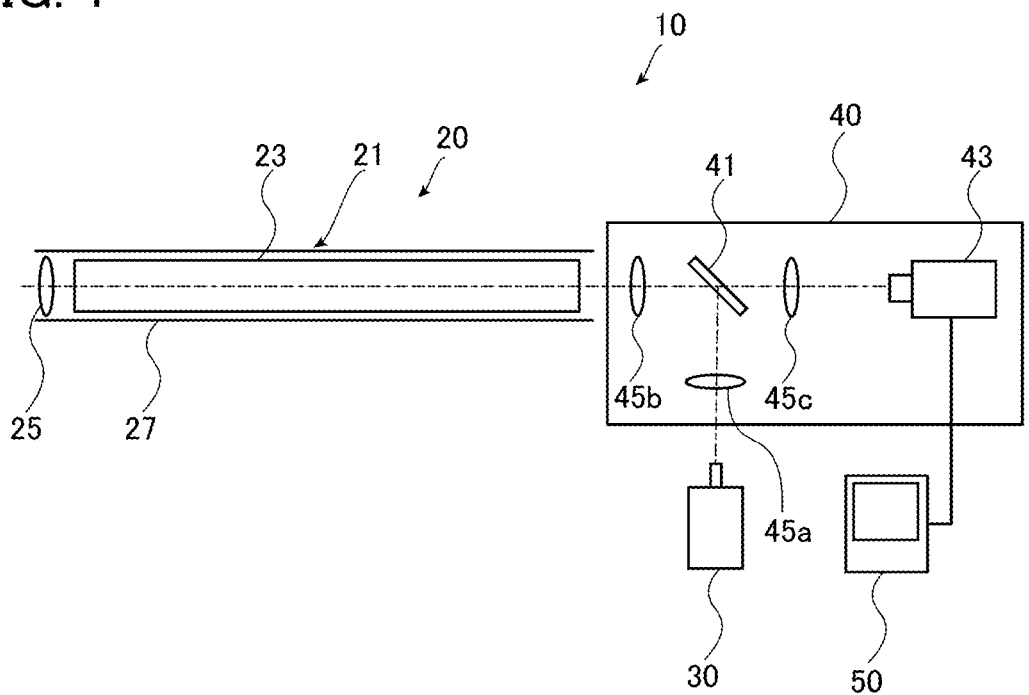
FIG. 1 is a diagram illustrating an endoscope system according to one or more embodiments of the present invention.

FIG. 1 is a diagram illustrating a schematic configuration of an endoscope system 10 according to one or more embodiments of the present invention. The endoscope system 10 includes, for example, an endoscope 20 used in an industrial field or a medical field. The endoscope 20 includes, for example, an elongated insertion portion 21 to be inserted into a subject in order to observe an object in the subject. Examples of the subject include a structure such as an engine and a body cavity.

The insertion portion 21 includes an elongated image fiber 23 disposed over the entire length of the insertion portion 21, an objective lens 25 disposed on the objective side of the image fiber 23, and a tubular member 27 that houses the image fiber 23 and the objective lens 25 in an internal space. The image fiber 23 is a member through which illumination light and imaging light propagate. For example, the illumination light is visible light that irradiates an object, and the wavelength of the visible light is 400 nm to 700 nm. In addition, the imaging light is reflected light reflected from the object irradiated with the illumination light. The objective lens 25 is disposed at a distal end of the insertion portion 21. In one or more embodiments, the tubular member 27 is made of, for example, a metal member such as stainless steel or a resin material. The tubular member 27 may be the outermost layer of the insertion portion 21 or may be one component disposed in the internal space of the insertion portion 21.

The endoscope system 10 further includes a light source portion 30 that emits the illumination light, and an optical system 40 optically connected to the light source portion 30 and the image fiber 23. The optical system 40 causes the illumination light from the light source portion 30 to be incident on the image fiber 23, and the imaging light emitted from the image fiber 23 is incident on the optical system 40. In addition, the endoscope system 10 further includes a display portion 50 that displays an image on the basis of an image signal generated from the imaging light by the optical system 40.

For example, an LED or the like is used as the light source portion 30. For example, a monitor or the like is used as the display portion 50. The display portion displays, for example, a still image or a moving image. The image is, for example, two-dimensional.

The optical system 40 is connected to the eyepiece side of the endoscope 20. The optical system 40 includes a wavelength filter 41 and an imaging portion 43. The wavelength filter 41 reflects at least a part of the illumination light emitted from the light source portion 30 to the image fiber 23. In addition, at least a part of the imaging light propagated from the image fiber 23 passes through the wavelength filter 41. The imaging portion 43 captures an image of the imaging light that has passed through the wavelength filter 41 and generates an image signal on the basis of the imaging light. The imaging portion 43 outputs the generated image signal to the display portion 50. For example, a CCD camera or the like is used as the imaging portion 43.

In addition, the optical system 40 further includes lenses 45a, 45b, and 45c disposed between the light source portion 30 and the wavelength filter 41, between the wavelength filter 41 and the image fiber 23, and between the wavelength filter 41 and the imaging portion 43. The lens 45a converts the illumination light traveling to the wavelength filter 41 into parallel light. For example, the lens 45b varies the cross-sectional region of the illumination light such that the illumination light reflected by the wavelength filter 41 is incident on light guide fibers 75 to be described below. In addition, the lens 45b converts the imaging light propagated from the image fiber 23 into parallel light. The lens 45c condenses the imaging light on the imaging portion 43.

Figure 2:
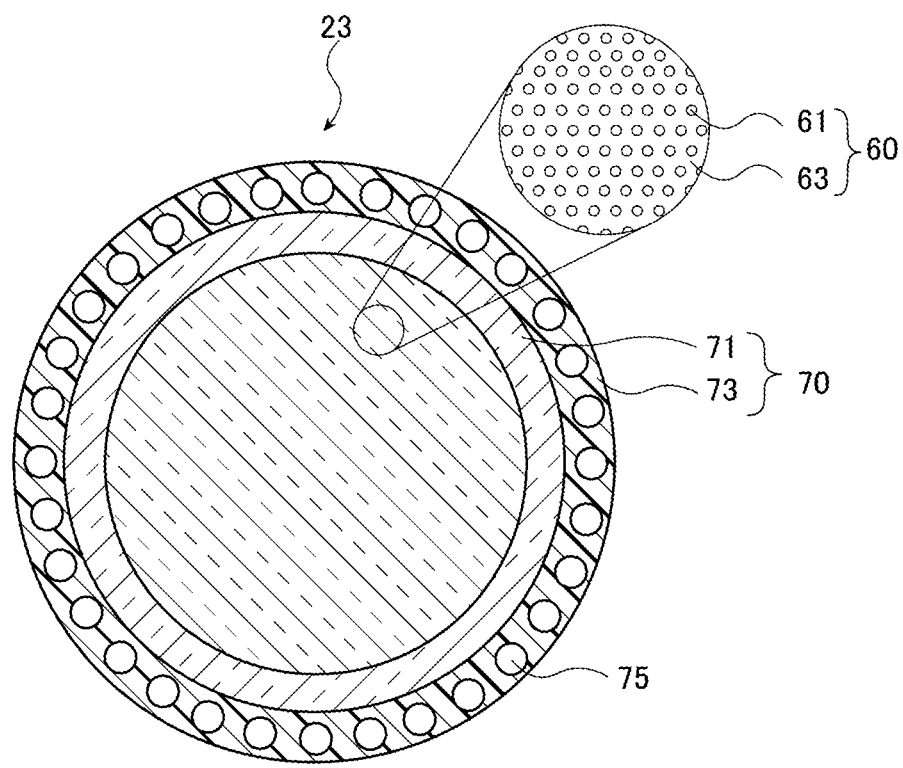
FIG. 2 is a cross-sectional diagram perpendicular to a longitudinal direction of an image fiber in the endoscope system of FIG. 1.

Next, the image fiber 23 will be described with reference to FIG. 2. FIG. 2 is a cross-sectional diagram perpendicular to the longitudinal direction of the image fiber 23 according to one or more embodiments.

The image fiber 23 includes an image fiber main body 60 through which the imaging light propagates toward the optical system 40, a plurality of light guide fibers 75 through which the illumination light propagates, and a light guide layer 70 covering the external peripheral surface of a cladding 63, which will be described below, of the image fiber main body 60 over the entire periphery and the entire length and through which the illumination light can propagate from the light guide fibers 75.

The shape of the cross-section perpendicular to the longitudinal direction of the image fiber main body 60 is, for example, a circular shape. The diameter of the image fiber main body 60 having a circular shape is, for example, 100 µm to 2500 µm.

The image fiber main body 60 is an elongated multicore fiber, and the multicore fiber has a plurality of cores 61 and the cladding 63 integrally enclosing the plurality of cores 61. When such image fiber main body 60 is manufactured, a plurality of elongated core-cladding optical fibers, which is not illustrated, is inserted into a quartz tube, which is not illustrated, in a bundled state and held in the quartz tube. When a plurality of optical fibers in a bundle is drawn together with the quartz tube, claddings of the plurality of optical fibers are softened and integrated with each other to form the common cladding 63. In addition, when the claddings of the plurality of optical fibers are softened and integrated with each other, the cladding 63 is fixed to an internal peripheral surface of the quartz tube, and the quartz tube becomes a quartz layer 71, which will be described below, which is a part of the light guide layer 70. Thus, the image fiber main body 60 integrated with the quartz layer 71 is configured.

In a cross-section perpendicular to the longitudinal direction of the image fiber main body 60, the cores 61 are disposed independently of each other, and the cladding 63 is formed continuously around the cores 61 and is in close contact with an external peripheral surface of the cores 61 without a gap. The cores 61 are disposed substantially uniformly throughout the cross-section perpendicular to the longitudinal direction of the image fiber main body 60. The uniform disposition means disposition over the entire region without deviation to a partial region of the cross-section of the image fiber main body 60. The interval between the cores 61 is substantially constant. However, the interval between the cores 61 may not be constant. In one or more embodiments, this interval is, for example, 1 to 1.2 times the outer diameter of the cores 61. Note that when a cross-section perpendicular to the longitudinal direction of the image fiber main body 60 is viewed, the cores 61 and the cladding 63 form an image circle.

The cores 61 constitute a pixel obtained by the image fiber 23. The number of cores 61 (the number of pixels) is, for example, 3000 pixels to 50000 pixels. In one or more embodiments, the cores 61 are made of, for example, quartz glass. For example, a dopant that increases a refractive index, such as germanium, is added to the quartz glass constituting the cores 61.

The cross-sectional shape of the cores 61 may be, for example, an isotropic shape such as a circular shape or a hexagonal shape, or may be a shape having anisotropy such as an elliptical shape, an oblong shape, a rectangular shape, or a rhombic shape. In the following description, it is assumed that the cores 61 have a circular shape. Each of the cores 61 having a circular shape has substantially the same outer diameter, and the outer diameter of the cores 61 having a circular shape is, for example, 3 μm to 5 μm. Note that the outer diameters of the cores 61 having a circular shape may be different from each other.

In one or more embodiments, the cladding 63 is made of, for example, quartz glass. A dopant such as fluorine may be added to the quartz glass constituting the cladding 63.

The light guide layer 70 of one or more embodiments includes the quartz layer 71 that covers the external peripheral surface of the cladding 63 over the entire periphery and the entire length, and a cover layer 73 that covers the external peripheral surface of the quartz layer 71 over the entire periphery and the entire length.

The quartz layer 71 is in close contact with the external peripheral surface of the cladding 63 without a gap by the fixation described above. Therefore, the quartz layer 71 covers the external peripheral surface of the cladding 63 over the entire periphery. The cross-sectional shape of the quartz layer 71 is a ring shape, and the thickness of the quartz layer 71 is, for example, 100 μm to 300 μm.

The cover layer 73 is made of, for example, resin such as silicone or polyimide. The cross-sectional shape of the cover layer 73 is a ring shape, and the thickness of the cover layer 73 is, for example, 30 μm to 400 μm. The thickness of the cover layer 73 made of resin is controlled at the time of manufacturing the image fiber 23.

The internal peripheral surface of the cover layer 73 is in close contact with the external peripheral surface of the quartz layer 71 without a gap. Therefore, the cover layer 73 covers the external peripheral surface of the cladding 63 over the entire periphery via the quartz layer 71. In addition, the external peripheral surface of the cover layer 73 is covered with the tubular member 27, and is adhered to the internal peripheral surface of the tubular member 27 by an adhesive, which is not illustrated. The cover layer 73 is also a protective member that buffers an external force acting from the outside and protects the image fiber main body 60, the quartz layer 71, and the light guide fibers 75 from the external force. The external force is, for example, a force acting on the image fiber 23 from the tubular member 27 when the insertion portion 21 is bent, a force acting on the image fiber 23 from an inner wall or the like in the subject through the tubular member 27 when the insertion portion 21 comes into contact with the inner wall, or the like.

The light guide fibers 75 are optically connected to the light source portion 30 via the optical system 40. The light guide fibers 75 are a member on and through which the illumination light emitted from the light source portion 30 is incident and propagates via the optical system 40. In this case, for example, the lens 45b varies the cross-sectional region of the illumination light so that the illumination light is incident on the light guide fibers 75 as described above. Note that the lens 45b may condense the illumination light so that the illumination light is incident on the light guide fibers 75. In addition, the light guide fibers 75 are optically connected to the light guide layer 70.

In one or more embodiments, the light guide fibers 75 are disposed inside the cover layer 73 along the longitudinal direction of the light guide layer 70. In other words, the light guide fibers 75 are not a member disposed in the internal space of the cover layer 73 having a ring shape, but are a member embedded in a thick portion of the cover layer 73. Therefore, the external peripheral surfaces of the light guide fibers 75 are in contact with the cover layer 73 inside the cover layer 73, and the light guide fibers 75 are protected from the external force described above by the cover layer 73.

In one or more embodiments, in the cross-section of the cover layer 73, the light guide fibers 75 embedded in the cover layer 73 are disposed substantially uniformly over the entire thick portion of the cover layer 73. The uniform disposition means disposition over the entire region without deviation to a partial region of the cross-section of the cover layer 73. The light guide fibers 75 may be disposed on the periphery of a concentric circle centered at the center of the cross-section of the cover layer 73. The light guide fibers 75 adjacent to each other in the circumferential direction are disposed apart from each other, but may be disposed in close contact with each other without a gap. When the light guide fibers 75 are separated from each other, the intervals between the light guide fibers 75 in the circumferential direction may be equal intervals, but may be different in one or more embodiments. The light guide fibers 75 may be disposed in layers in the thickness direction of the cover layer 73. The light guide fibers 75 are disposed away from the quartz layer 71, but may be disposed in contact with the quartz layer 71.

The cover layer 73 may be molded into a sheet shape in a state where the light guide fibers 75 are disposed inside the cover layer 73, and then may be longitudinally attached to the external peripheral surface side of the quartz layer 71 and in close contact with the external peripheral surface of the quartz layer 71. Alternatively, after the light guide fibers 75 are longitudinally attached to the external peripheral surface of the quartz layer 71, the light guide fibers 75 and the quartz layer 71 may be impregnated and covered with the cover layer 73, which is resin.

In addition, in one or more embodiments, the light guide fibers 75 are disposed from one end of the cover layer 73 to the other end of the cover layer 73 along the longitudinal direction of the light guide layer 70. The one end is on the optical system 40 side, and the other end is an emission end irradiated with the illumination light and is on the objective lens 25 side.

The light guide fibers 75 are made of, for example, plastic, and ensure resistance to bending of the image fiber 23. A cross-sectional shape of the light guide fibers 75 is, for example, a circular shape. The diameter of the light guide fibers 75 is, for example, 30 μm or more.

Figure 3:
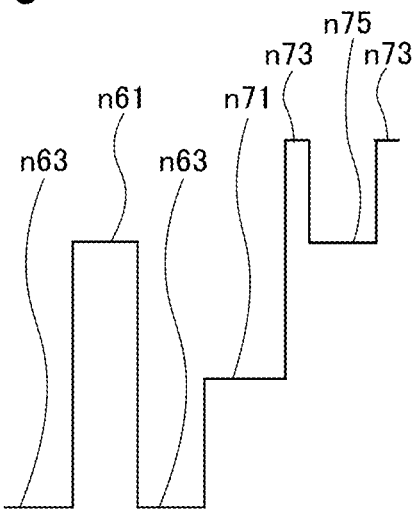
FIG. 3 is a diagram illustrating a refractive index profile in the image fiber illustrated in FIG. 2.

Here, the refractive index profile in the image fiber 23 will be described with reference to FIG. 3. FIG. 3 is a diagram illustrating a refractive index profile in the image fiber 23. In FIG. 3, the vertical axis represents a relative difference in refractive index between the respective members in the image fiber 23, and the horizontal axis in FIG. 3 represents a simplified positional relationship between the respective members.

As illustrated in FIG. 3, in the image fiber main body 60, a refractive index n63 of the cladding 63 is lower than a refractive index n61 of the cores 61. A refractive index n71 of the quartz layer 71 is lower than the refractive index n61 of the cores 61 and higher than the refractive index n63 of the cladding 63. In FIG. 3, a refractive index n75 of the light guide fibers 75 is higher than the refractive index n71 of the quartz layer 71 and lower than a refractive index n73 of the cover layer 73. Note that the refractive index n75 of the light guide fibers 75 may be the same as the refractive index n73 of the cover layer 73. In the example of FIG. 3, the refractive index n75 of the light guide fibers 75 is the same as the refractive index n61 of the cores 61, but may be higher or lower than the refractive index n61 of the cores 61. The refractive index n73 of the cover layer 73 is higher than the refractive index n63 of the cladding 63 and the refractive index n71 of the quartz layer 71.

Next, an operation of the endoscope system 10 will be described.

The insertion portion 21 of the endoscope 20 is inserted, the distal end of the insertion portion 21 first, into the subject, and the objective lens 25 is directed to the object. The illumination light is emitted from the light source portion 30 toward the optical system 40, and is reflected by the wavelength filter 41 of the optical system 40 toward the image fiber 23. Then, the illumination light is incident on the light guide fibers 75 of the image fiber 23 from the optical system 40 and propagates through the light guide fibers 75.

The refractive index n75 of the light guide fibers 75 of one or more embodiments is lower than the refractive index n73 of the cover layer 73. In this case, a part of the illumination light propagating through the light guide fibers 75 propagates from the light guide fibers 75 to the cover layer 73, and further propagates through the cover layer 73. In addition, another part of the illumination light propagates through the light guide fibers 75 disposed from one end to the other end of the cover layer 73 along the longitudinal direction of the light guide layer 70. In addition, the refractive index n71 of the quartz layer 71 is lower than the refractive index n73 of the cover layer 73 and the refractive index n75 of the light guide fibers 75. Therefore, the illumination light propagates through the cover layer 73 and the light guide fibers 75 in a state where leakage from the cover layer 73 and the light guide fibers 75 to the quartz layer 71 is suppressed.

Then, the illumination light passes through the objective lens 25, is emitted from the distal end of the insertion portion 21 toward the object, and is emitted to the object.

The imaging light, which is reflected light from the object, is incident on the cores 61 of the image fiber main body 60 via the objective lens 25. Since the refractive index n61 of the cores 61 is higher than the refractive index n63 of the cladding 63 and the refractive index n71 of the quartz layer 71, most of the imaging light propagates through the cores 61 without leakage from the cores 61 to the cladding 63 and the quartz layer 71. The imaging light travels from the image fiber main body 60 to the optical system 40, passes through the wavelength filter 41, and is captured by the imaging portion 43. The imaging portion 43 generates an image signal on the basis of the imaging light and outputs the image signal to the display portion 50. The display portion 50 displays an image of the object on the basis of the image signal.

As described above, the image fiber 23 of one or more embodiments includes the plurality of cores 61, the cladding 63 integrally enclosing the plurality of cores 61, the plurality of light guide fibers 75 through which the illumination light propagates, and the light guide layer 70 covering the external peripheral surface of the cladding 63 over the entire periphery and in contact with the external peripheral surface of the light guide fibers 75, the light guide layer 70 being capable of propagating the illumination light from the light guide fibers 75. Note that, in one or more embodiments, the plurality of light guide fibers 75 is disposed, but at least one light guide fiber 75 may be disposed.

In such image fiber 23, since the illumination light propagates through the light guide fibers 75 and can propagate from the light guide fibers 75 to the light guide layer 70, the illumination light can propagate through the entire region of the cross-section of the light guide layer 70 covering the external peripheral surface of the cladding 63 over the entire periphery. Therefore, with the image fiber 23, uneven irradiation of the illumination light can be suppressed.

In addition, since the illumination light propagates through the light guide fibers 75 and propagates through the cover layer 73 and is emitted from the light guide fibers 75 and the cover layer 73, the emission range of the illumination light can be expanded as compared with the case where the illumination light is emitted only from the light guide fibers 75. In addition, in the image fiber 23 of one or more embodiments, the illumination light is incident on the cover layer 73 from the light source portion 30 via the optical system 40 and the light guide fibers 75. Therefore, the illumination light can be easily incident on the cover layer 73 as compared with the case where the illumination light is incident on the cover layer 73 from the light source portion 30 via the optical system 40.

In addition, even when bending occurs in the image fiber 23 due to bending of the insertion portion 21 inserted into the subject, the light guide layer 70 is not separated from the external peripheral surface of the cladding 63 so that wobbling is suppressed and is in a state of being stably disposed with respect to the cladding 63. Thus, displacement of the emission position of the illumination light at the distal end of the insertion portion 21 is suppressed, and the illumination light can be stably emitted toward the object. Therefore, with the image fiber 23, the illumination light can be emitted stably.

In addition, in the image fiber 23 of one or more embodiments, the light guide layer 70 has the cover layer 73 made of resin, the refractive index n73 of the cover layer 73 is higher than the refractive index n63 of the cladding 63 and the refractive index n75 of the light guide fibers 75, and the light guide fibers 75 are disposed inside the cover layer 73 along the longitudinal direction of the light guide layer 70. Note that, in the image fiber 23 of one or more embodiments, the light guide fibers 75 may be disposed in at least a part of the inside of the cover layer 73. The part indicates, for example, a portion from one end of the cover layer 73 to a portion between the one end of the cover layer 73 and the other end of the cover layer 73. In addition, as described above, the refractive index n73 of the cover layer 73 may be the same as the refractive index n75 of the light guide fibers 75.

The flexibility of the cover layer 73 made of resin is generally superior to the flexibility of a layer made of glass. Therefore, the cover layer 73 is resistant to bending and is in close contact with the external peripheral surface of the cladding 63 or the like to be in a state of being more stably disposed. Thus, displacement of the emission position of the illumination light is further suppressed, and the illumination light can be more stably emitted toward the object. Therefore, with the image fiber 23, the illumination light can be emitted more stably.

In addition, when the refractive index n73 of the cover layer 73 is higher than the refractive index n63 of the cladding 63, propagation of the illumination light from the cover layer 73 to the cladding 63 can be suppressed. Therefore, with the image fiber 23, waste of the illumination light can be suppressed. In addition, when the refractive index n73 of the cover layer 73 is equal to or higher than the refractive index n75 of the light guide fibers 75, the illumination light easily propagates from the light guide fibers 75 to the cover layer 73, a part of the illumination light propagates from the light guide fibers 75 to the cover layer 73 and further propagates through the cover layer 73, and in addition, another part of the illumination light can propagate through the light guide fibers 75. Therefore, with the image fiber 23, the illumination light can be more efficiently propagated to the light guide fibers 75 by the cover layer 73. In addition, since the illumination light propagates through the cover layer 73 and is emitted from the cover layer 73, the emission range of the illumination light can be expanded as compared with the case where the illumination light is emitted only from the light guide fibers 75, and uneven irradiation of the illumination light can be suppressed.

When the light guide fibers 75 are disposed in at least a part of the inside of the cover layer 73, displacement of the light guide fibers 75 with respect to the cover layer 73 is suppressed, and the light guide fibers 75 are in a state of being stably disposed. In addition, when the light guide fibers 75 are disposed in at least a part of the inside of the cover layer 73, the illumination light can propagate from the entire periphery of the external peripheral surface of the light guide fibers 75 to the cover layer 73. Therefore, with the image fiber 23, uneven irradiation of the illumination light can be suppressed.

In addition, in general, the thickness of the cover layer 73 is controlled at the time of manufacturing the image fiber 23 and can be easily reduced. Therefore, with the image fiber 23 of one or more embodiments, the image fiber 23 can be easily reduced in diameter.

In addition, since the light guide fibers 75 are disposed not on the external peripheral surface of the cover layer 73 but in at least a part of the inside of the cover layer 73, with the image fiber 23, an increase in diameter of the image fiber 23 can be prevented. In addition, in general, the light guide fibers 75 through which the illumination light propagates has light propagation efficiency superior to that of the cover layer 73. Therefore, with the image fiber 23 of one or more embodiments, brighter illumination light can be emitted.

In addition, since the light guide fibers 75 are disposed inside the cover layer 73, interference between the light guide fibers 75 and the quartz layer 71 can be suppressed. Therefore, breakage of the light guide fibers 75 and the quartz layer 71 due to interference can be suppressed. The light guide fibers 75 are not glass but plastic, and the quartz layer 71 is glass. Therefore, even when interference between the quartz layer 71 and the light guide fibers 75 occurs, rubbing of glasses does not occur, and breakage between the quartz layer 71 and the light guide fibers 75 can be suppressed. When the light guide fibers 75 are plastic as described above, the image fiber 23 can ensure flexibility, and resistance of the image fiber 23 to bending of the image fiber 23 can be ensured. In addition, in a case where the image fiber 23 is connected to the optical system 40 by a connector, which is not illustrated, or the like, when the light guide fibers 75 are disposed inside the cover layer 73, coming apart of the light guide fibers 75 is suppressed, and a connection operation by the connector or the like can be facilitated.

In addition, with the image fiber 23 of one or more embodiments, the light guide fibers 75 are disposed from one end to the other end of the cover layer 73 along the longitudinal direction of the light guide layer 70. In this case, the cover layer 73 can efficiently propagate the illumination light from one end to the other end of the cover layer 73 by the light guide fibers 75. Thus, a part of the illumination light can propagate through the cover layer 73, and in addition, another part of the illumination light can propagate through the light guide fibers 75. Therefore, with the image fiber 23 of one or more embodiments, the illumination light can be efficiently propagated, and uneven irradiation of the illumination light can be suppressed.

In addition, in one or more embodiments, the endoscope 20 includes the insertion portion 21 to be inserted into the subject, and the image fiber 23 described above to be disposed in the internal space of the insertion portion 21. In the endoscope 20, the uneven irradiation of the illumination light can be suppressed, and the endoscope 20 can irradiate the object in the subject with the illumination light with suppressed uneven irradiation.

In addition, in one or more embodiments, the endoscope system 10 includes the endoscope 20 described above and the light source portion 30 that emits the illumination light. In addition, the endoscope system 10 further includes the optical system 40 that propagates the illumination light emitted from the light source portion 30 toward the light guide fibers 75, and captures an image of the imaging light that is reflected light reflected from the object irradiated with the illumination light and has propagated through the cores 61, and the display portion 50 that displays an image on the basis of the imaging light captured by the optical system 40. In the endoscope system 10, the endoscope 20 can irradiate the object with the illumination light with suppressed uneven irradiation, the display portion 50 can display the image of the object in which the uneven irradiation is suppressed.

Next, embodiments of the present invention will be described in detail with reference to FIGS. 4 and 5. Note that the same or equivalent components as those of the above-described embodiments are designated by the same reference numerals and duplicated description will be omitted unless otherwise specified.

Figure 4:
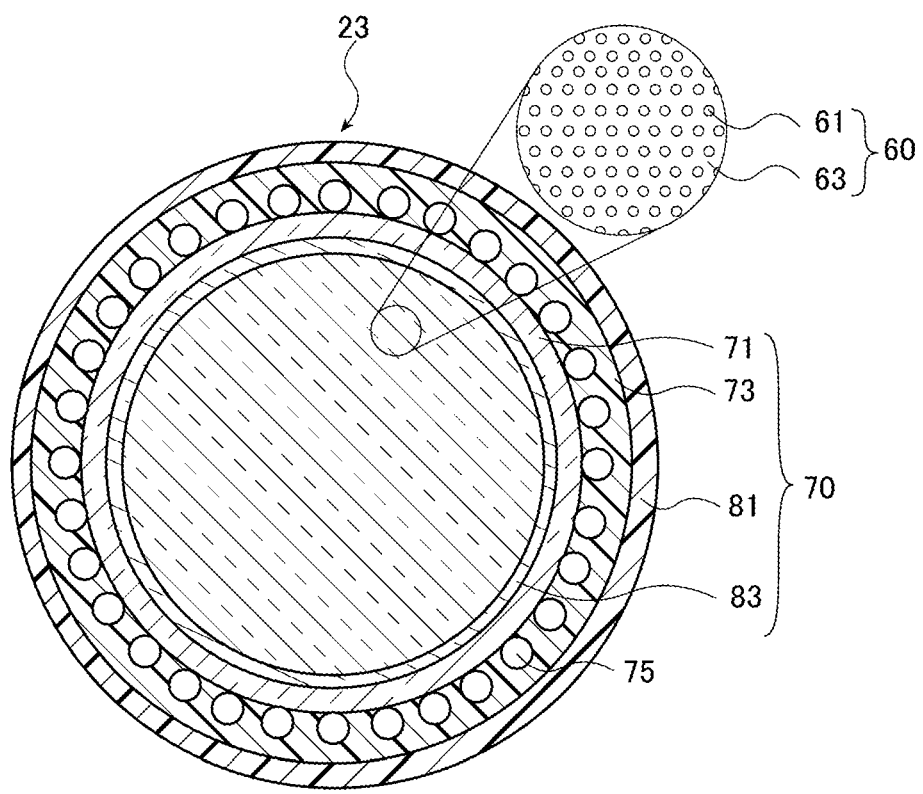
FIG. 4 is a cross-sectional diagram perpendicular to a longitudinal direction of an image fiber according to one or more embodiments of the present invention.
Figure 5:
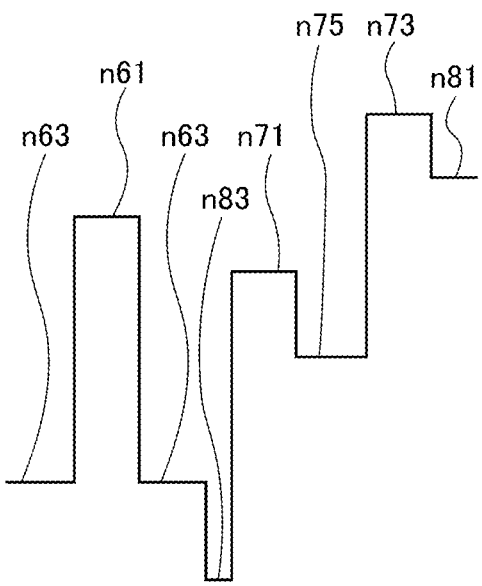
FIG. 5 is a diagram illustrating a refractive index profile in the image fiber illustrated in FIG. 4.

FIG. 4 is a cross-sectional diagram perpendicular to the longitudinal direction of the image fiber 23 according to one or more embodiments. In the image fiber 23 of one or more embodiments, the configuration of a light guide layer 70 is different from the configuration of the light guide layer 70 of the above-described embodiments, the position of light guide fibers 75 is different from the position of the light guide fibers 75 of the above-described embodiments, and the refractive index profile in an image fiber 23 is different from the refractive index profile in the image fiber 23 of the above-described embodiments.

In the image fiber 23 of one or more embodiments, the light guide layer 70 further has an outer low refractive index layer 81 covering the external peripheral surface of a cover layer 73 over the entire periphery and the entire length. The cross-sectional shape of the outer low refractive index layer 81 is, for example, a ring shape, and the internal peripheral surface of the outer low refractive index layer 81 is in close contact with the external peripheral surface of the cover layer 73 without a gap. In addition, the external peripheral surface of the outer low refractive index layer 81 is covered with the internal peripheral surface of a tubular member 27, and is adhered to the internal peripheral surface of the tubular member 27 by an adhesive, which is not illustrated. The outer low refractive index layer 81 is made of, for example, resin different from the cover layer 73. The resin of the outer low refractive index layer 81 is, for example, applied onto the external peripheral surface of the cover layer 73 and then cured.

In addition, in the image fiber 23 of one or more embodiments, the light guide layer 70 further has an inner low refractive index layer 83 disposed between a cladding 63 and a quartz layer 71. The cross-sectional shape of the inner low refractive index layer 83 is a ring shape, and the external peripheral surface of the inner low refractive index layer 83 is covered with the internal peripheral surface of the quartz layer 71 and is in close contact with the internal peripheral surface of the quartz layer 71 without a gap. The internal peripheral surface of the inner low refractive index layer 83 covers the external peripheral surface of the cladding 63 and is in close contact with the external peripheral surface of the cladding 63 without a gap. The thickness of the inner low refractive index layer 83 is, for example, 2 μm to 20 μm.

For example, when an image fiber main body 60 is manufactured, the inner low refractive index layer 83 is disposed on the internal peripheral surface of a quartz tube in advance before a plurality of bundled core-cladding optical fibers is inserted into the quartz tube. The inner low refractive index layer 83 is made of, for example, quartz, which is a member different from the quartz layer 71, to which a dopant for reducing the refractive index such as fluorine is added.

In addition, the light guide fibers 75 of one or more embodiments are disposed on at least a part of the external peripheral surface of the quartz layer 71 along a longitudinal direction of the light guide layer 70. With a part of the external peripheral surface of the light guide fibers 75 in a state of being in contact with the external peripheral surface of the quartz layer 71, the remaining part of the external peripheral surface of the light guide fibers 75 is covered with the cover layer 73. For example, the light guide fibers 75 are disposed from one end to the other end of the quartz layer 71 along the longitudinal direction of the light guide layer 70.

Here, the refractive index profile in the image fiber 23 of one or more embodiments will be described with reference to FIG. 5. FIG. 5 is a diagram illustrating a refractive index profile in the image fiber 23. In FIG. 5, the vertical axis represents a relative difference in refractive index between the respective members in the image fiber 23, and the horizontal axis in FIG. 5 represents a simplified positional relationship between the respective members.

In the image fiber 23 of one or more embodiments, a refractive index $n81$ of the outer low refractive index layer 81 is lower than a refractive index $n73$ of the cover layer 73. In addition, the refractive index $n71$ of the quartz layer 71 is higher than a refractive index $n75$ of the light guide fibers 75. The refractive index $n71$ of the quartz layer 71 may be the same as the refractive index $n75$ of the light guide fibers 75. A refractive index $n83$ of the inner low refractive index layer 83 is lower than a refractive index $n63$ of the cladding 63 and the refractive index $n71$ of the quartz layer 71.

Next, propagation of the illumination light through the light guide fibers 75 and the light guide layer 70 will be described.

Similar to the above-described embodiments, a part of the illumination light propagating through the light guide fibers 75 propagates from the light guide fibers 75 to the cover layer 73, and further propagates through the cover layer 73. In addition, another part of the illumination light propagates through the light guide fibers 75.

In one or more embodiments, the outer low refractive index layer 81 covers the external peripheral surface of the cover layer 73 over the entire periphery, and the refractive index $n81$ of the outer low refractive index layer 81 is lower than the refractive index $n73$ of the cover layer 73. Thus, the illumination light propagating through the cover layer 73 is easily confined in the cover layer 73 by the outer low refractive index layer 81, and can propagate through the cover layer 73 in a state where leakage from the cover layer 73 to the outside of the image fiber 23 is suppressed. Therefore, with the image fiber 23 of one or more embodiments, the illumination light can be more efficiently propagated.

In addition, the light guide fibers 75 are disposed on at least a part of the external peripheral surface of the quartz layer 71 along the longitudinal direction of the light guide layer 70. Thus, a part of the illumination light propagating through the light guide fibers 75 propagates from the light guide fibers 75 to the quartz layer 71, and further propagates through the quartz layer 71. Therefore, with the image fiber 23, uneven irradiation of the illumination light can be suppressed. In addition, the refractive index $n71$ of the quartz layer 71 is higher than the refractive index $n63$ of the cladding. Thus, propagation of the illumination light from the quartz layer 71 to the cladding 63 is suppressed. Therefore, with the image fiber 23, waste of the illumination light can be suppressed.

In addition, the light guide fibers 75 are disposed from one end to the other end of the quartz layer 71 along the longitudinal direction of the light guide layer 70. In this case, the light guide layer 70 can efficiently propagate the illumination light from one end to the other end of the quartz layer 71 by the light guide fibers 75. Therefore, with the image fiber 23, the illumination light can be efficiently propagated.

In addition, the refractive index $n71$ of the quartz layer 71 is equal to or higher than the refractive index $n75$ of the light guide fibers 75. In this case, the illumination light easily propagates from the light guide fibers 75 to the quartz layer 71, and a part of the illumination light can propagate from the light guide fibers 75 to the quartz layer 71 and further propagate through the quartz layer 71. In addition, another part of the illumination light can propagate through the light guide fibers 75. Therefore, with the image fiber 23, the illumination light can be efficiently propagated to the quartz layer 71 by the light guide fibers 75, and the illumination light is propagated through the quartz layer 71 and emitted from the quartz layer 71. Therefore, the emission range of the illumination light can be expanded as compared with the case where the illumination light is emitted only from the light guide fibers 75, and uneven irradiation of the illumination light can be suppressed.

In addition, the internal peripheral surface of the quartz layer 71 is in close contact with the external peripheral surface of the inner low refractive index layer 83 without a gap, and the internal peripheral surface of the inner low refractive index layer 83 is in close contact with the external peripheral surface of the cladding 63 without a gap. Thus, even when bending occurs in the image fiber 23 due to bending of the insertion portion 21 inserted into the subject, the quartz layer 71, which is integral with the cladding 63 via the inner low refractive index layer 83, is in a state of being stably disposed. In addition, displacement of the emission position of the illumination light at the distal end of the insertion portion 21 is further suppressed, and the illumination light can be more stably emitted toward the object. Therefore, with the image fiber 23, the illumination light can be emitted stably.

In addition, the refractive index n83 of the inner low refractive index layer 83 inner is lower than the refractive index n63 of the cladding 63 and the refractive index n71 of the quartz layer 71. When the image fiber 23 is viewed from the viewpoint of the refractive index, the inner low refractive index layer 83 has a groove shape, and the image fiber 23 has a trench structure. With such trench structure, the illumination light is easily confined in the quartz layer 71 by the inner low refractive index layer 83, and can propagate through the quartz layer 71 in a state where leakage from the quartz layer 71 to the cores 61 and the cladding 63 is suppressed. Therefore, with the image fiber 23 of one or more embodiments, the illumination light can be efficiently propagated.

Next, embodiments of the present invention will be described in detail with reference to FIG. 6. Note that the same or equivalent components as those of the above-described embodiments are designated by the same reference numerals and duplicated description will be omitted unless otherwise specified.

Figure 6:
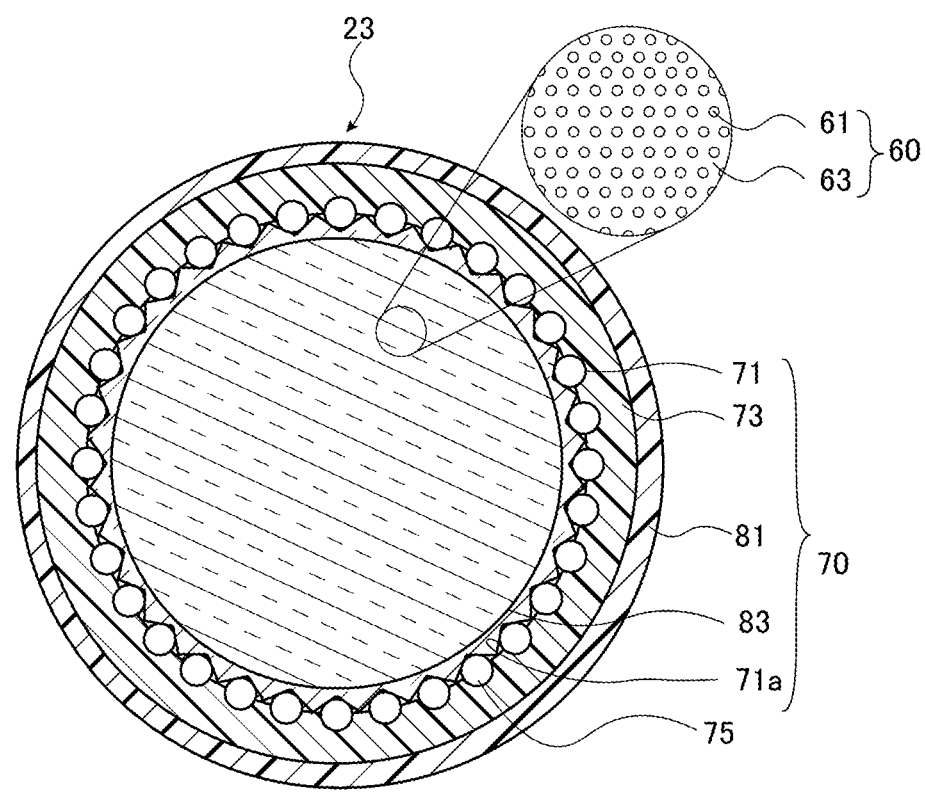
FIG. 6 is a cross-sectional diagram perpendicular to a longitudinal direction of an image fiber according to one or more embodiments of the present invention.

FIG. 6 is a cross-sectional diagram perpendicular to the longitudinal direction of an image fiber 23 according to one or more embodiments. In the image fiber 23 of one or more embodiments, the configuration of a light guide layer 70 is different from the configuration of the light guide layer 70 of the above-described embodiments.

A quartz layer 71 of one or more embodiments has at least one groove 71a provided in at least a part of the external peripheral surface of the quartz layer 71 along the longitudinal direction of the light guide layer 70. The groove 71a is mechanically disposed in the quartz layer 71 by cutting, for example, by a lathe or milling cutter. At least a part of at least one light guide fiber 75 in the radial direction is disposed in the groove 71a.

In the cross-sectional shape of the quartz layer 71, the shape of the groove 71a may be any shape that the light guide fiber 75 can be received, for example, a V shape, a concave shape, or the like. In the relationship between the depth of the groove 71a and the diameter of the light guide fiber 75, a part of the light guide fiber 75 may be accommodated in the groove 71a, and the remaining part of the light guide fiber 75 may protrude outward from the external peripheral surface of the quartz layer 71. Note that when the entire light guide fiber 75 is accommodated in the groove 71a, the image fiber 23 can be reduced in diameter. The light guide fiber 75 may be fixed in the groove 71a by the resin of the cover layer 73, or may be fixed to the groove 71a by an adhesive, which is not illustrated.

The light guide fiber 75 in the groove 71a is disposed from one end to the other end of the quartz layer 71 along the longitudinal direction of the quartz layer 71, similarly to the light guide fibers 75 embedded in the cover layer 73 of the above-described embodiments.

In one or more embodiments, when at least a part of the light guide fiber 75 in the radial direction is disposed in the groove 71a, the light guide fiber 75 is in a state of being stably disposed with respect to the quartz layer 71. Thus, even when bending occurs in the image fiber 23 due to bending of an insertion portion 21 inserted into the subject, displacement of the emission position of the illumination light at the distal end of the insertion portion 21 is further suppressed, and the illumination light can be stably emitted toward the object. Therefore, with the image fiber 23 of one or more embodiments, the illumination light can be emitted more stably.

In addition, since the light guide fiber 75 is disposed not on the external peripheral surface of the quartz layer 71 but in at least a part of the groove 71a, an increase in diameter of the image fiber 23 can be prevented in the image fiber 23. In addition, the light guide fiber 75 can be easily positioned by the groove 71a. Therefore, with the image fiber 23 of one or more embodiments, the image fiber 23 can be easily manufactured, and the emission position of the illumination light emitted from the image fiber 23 can be controlled.

Although the present invention has been described above by taking the aforementioned embodiments as an example, the present invention is not limited thereto, but can be changed appropriately.

For example, in one or more embodiments, the cover layer 73 may be optically connected to the optical system 40, and the illumination light may directly travel to the cover layer 73 from the optical system 40. Similarly, in one or more embodiments, the cover layer 73 may be optically connected to the optical system 40, and the illumination light may directly travel to the cover layer 73 from the optical system 40. In addition, the light guide fibers 75 may protrude from the light guide layer 70 and extend toward the light source portion 30, and may be optically directly connected to the light source portion 30.

In addition, in one or more embodiments, the light guide fibers 75 disposed in the cover layer 73 may be disposed in a part of the cover layer 73 in the longitudinal direction. In one or more embodiments, the light guide fibers 75 are disposed from an end portion on a side where light is incident on the light guide layer 70 to the middle of the cover layer 73 in the longitudinal direction. In this case, the illumination light incident on the light guide fibers 75 can propagate from the light guide fibers 75 to the cover layer 73 in the middle of the cover layer 73 in the longitudinal direction, and can be emitted from the cover layer 73.

In addition, in one or more embodiments, the light guide fiber 75 disposed in the groove 71a may be disposed in a part of the quartz layer 71 in the longitudinal direction. In one or more embodiments, the light guide fiber 75 is disposed from an end portion on a side where light is incident on the light guide layer 70 to the middle of the quartz layer 71 in the longitudinal direction.

In addition, in one or more embodiments, at least one of the configuration in which the quartz layer 71 propagates the illumination light, the outer low refractive index layer 81, and the inner low refractive index layer 83 may be incorporated in the image fiber of the above-described embodiments.

In addition, in one or more embodiments, when the refractive index n71 of the quartz layer 71 and the refractive index n73 of the cover layer 73 are higher than the refractive index n75 of the light guide fibers 75, the refractive index n71 of the quartz layer 71 may be equal to, higher than, or lower than the refractive index n73 of the cover layer 73.

In addition, the groove 71a and the light guide fiber 75 disposed in the groove 71a described in the above-described embodiments may be incorporated in the image fibers of another above-described embodiment.

The endoscope 20 may be a flexible endoscope in which the insertion portion 21 has flexibility, or may be a rigid endoscope in which the insertion portion 21 maintains a straight state and has resistance to bending.

According to one or more embodiments of the present invention, an image fiber capable of stably emitting illumination light, an endoscope having the image fiber, and an endoscope system having the endoscope are provided, and can be used in various industries such as an industrial field and a medical field.

Although the disclosure has been described with respect to only a limited number of embodiments, those skilled in the art, having benefit of this disclosure, will appreciate that various other embodiments may be devised without departing from the scope of the present invention. Accordingly, the scope of the invention should be limited only by the attached claims.

The invention claimed is:

1. An image fiber comprising:
   a plurality of cores;
   a cladding that integrally encloses the plurality of cores;
   a light guide fiber that propagates illumination light; and
   a light guide layer that covers an entire periphery of an external peripheral surface of the cladding and that is in contact with an external peripheral surface of the light guide fiber, wherein
   the light guide layer propagates the illumination light from the light guide fiber,
   the light guide layer includes a cover layer made of resin,
   a refractive index of the cover layer is higher than a refractive index of the cladding and is equal to or higher than a refractive index of the light guide fiber, and
   the light guide fiber is at least partially disposed inside of the cover layer along a longitudinal direction of the light guide layer.

2. The image fiber according to claim 1, wherein the light guide fiber is disposed from one end to another end of the cover layer along the longitudinal direction of the light guide layer.

3. The image fiber according to claim 1, wherein
   the light guide layer further includes an outer low refractive index layer covering an external peripheral surface of the cover layer over an entire periphery, and
   a refractive index of the outer low refractive index layer is lower than the refractive index of the cover layer.

4. The image fiber according to claim 1, wherein
   the light guide layer includes a quartz layer having a refractive index higher than the refractive index of the cladding and equal to or higher than the refractive index of the light guide fiber, and
   the light guide fiber is at least partially disposed on an external peripheral surface of the quartz layer along a longitudinal direction of the light guide layer.

5. The image fiber according to claim 4, wherein the light guide fiber is disposed from one end to another end of the quartz layer along the longitudinal direction of the light guide layer.

6. The image fiber according to claim 4, wherein
   the light guide layer further includes an inner low refractive index layer disposed between the cladding and the quartz layer, and
   a refractive index of the inner low refractive index layer is lower than the refractive index of the cladding.

7. The image fiber according to claim 4, wherein
   the quartz layer has a groove at least partially disposed in the external peripheral surface of the quartz layer along the longitudinal direction of the light guide layer, and
   a part of the light guide fiber in a radial direction is disposed in the groove.

8. An endoscope comprising:
   an insertion portion that is inserted into a subject, and
   the image fiber according to claim 1 that is disposed in an internal space of the insertion portion.

9. An endoscope system comprising:
   the endoscope according to claim 8;
   a light source that emits the illumination light;
   an optical system that:
      propagates the illumination light emitted from the light source portion toward the light guide fiber and
      captures an image of imaging light that is reflected from an object irradiated with the illumination light and propagates through the cores; and
   a display that displays an image based on the imaging light captured by the optical system.

10. The image fiber according to claim 1, wherein
    the resin propagates the illumination light from the light guide fiber.

11. An image fiber comprising:
    a plurality of cores;
    a cladding that integrally encloses the plurality of cores;
    a light guide fiber that propagates illumination light; and
    a light guide layer that covers an entire periphery of an external peripheral surface of the cladding and that is in contact with an external peripheral surface of the light guide fiber, wherein
    the light guide layer propagates the illumination light from the light guide fiber,
    the light guide layer includes a quartz layer having a refractive index higher than the refractive index of the cladding and equal to or higher than the refractive index of the light guide fiber, and
    the light guide fiber is at least partially disposed on an external peripheral surface of the quartz layer along a longitudinal direction of the light guide layer.

12. The image fiber according to claim 11, wherein the light guide fiber is disposed from one end to another end of the quartz layer along the longitudinal direction of the light guide layer.

13. The image fiber according to claim 11, wherein
    the light guide layer further includes an inner low refractive index layer disposed between the cladding and the quartz layer, and
    a refractive index of the inner low refractive index layer is lower than the refractive index of the cladding.

14. The image fiber according to claim 11, wherein
    the quartz layer has a groove at least partially disposed in the external peripheral surface of the quartz layer along the longitudinal direction of the light guide layer, and
    a part of the light guide fiber in a radial direction is disposed in the groove.

* * * * *